US011583208B2

(12) United States Patent
Moore et al.

(10) Patent No.: US 11,583,208 B2
(45) Date of Patent: Feb. 21, 2023

(54) SYSTEMS AND DEVICES FOR DETECTING, LOCATING AND MITIGATING CONCUSSIVE IMPACT FORCES

(71) Applicants: Ryan David George Moore, Markham (CA); Timothy David Moore, Markham (CA)

(72) Inventors: Ryan David George Moore, Markham (CA); Timothy David Moore, Markham (CA)

(73) Assignee: BRAINBAG INC., Sudbury (CA)

( * ) Notice: Subject to any disclaimer, the term of this patent is extended or adjusted under 35 U.S.C. 154(b) by 294 days.

(21) Appl. No.: 16/385,727

(22) Filed: Apr. 16, 2019

(65) Prior Publication Data

US 2019/0313946 A1 Oct. 17, 2019

Related U.S. Application Data

(60) Provisional application No. 62/761,974, filed on Apr. 16, 2018.

(51) Int. Cl.
*A61B 5/103* (2006.01)
*A61B 5/11* (2006.01)
(Continued)

(52) U.S. Cl.
CPC ............. *A61B 5/11* (2013.01); *A42B 1/241* (2013.01); *A42B 1/242* (2013.01); *A42B 1/245* (2013.01);
(Continued)

(58) Field of Classification Search
CPC . A61B 5/11; A61B 5/6803; A61B 2562/0219; A42B 1/241; A42B 1/242; A42B 3/0433; A42B 3/06; A42B 3/30
See application file for complete search history.

(56) References Cited

U.S. PATENT DOCUMENTS

2004/0006312 A1\* 1/2004 Donnan .............. A61M 5/1782
604/181
2005/0278836 A1\* 12/2005 Nelson ................ A41D 13/015
2/455

(Continued)

OTHER PUBLICATIONS

Kuehn et al. Rodent Model of Direct Cranial Blast Injury. Journal of Neurotrauma Oct. 2011 (pp. 2155-2169) [retrieved on Nov. 30, 2020], Retrieved from <https://www.liebertpub.com/doi/full/10.1089/neu.2010.1532>.

(Continued)

*Primary Examiner* — Daniel L Cerioni
(74) *Attorney, Agent, or Firm* — Bereskin & Parr LLP

(57) ABSTRACT

Systems for detecting, locating and mitigating impact forces directed towards a person's head are described herein. The systems include devices for wearing on a wearer's head. The devices include a base configured to conform to the wearer's head and retain a plurality of pouches on an outer surface of the base. The plurality of pouches are configured to absorb at least a portion of the impact force directed towards the outer surface of the base, provide an indication when the impact force directed towards the outer surface of the base has a magnitude exceeding a concussion-indicating level of force, and provide a location of impact when the impact force directed towards the outer surface of the base has a magnitude exceeding the concussion-indicating level of force.

20 Claims, 5 Drawing Sheets

(51) Int. Cl.
  *A61B 5/00* (2006.01)
  *A42B 3/30* (2006.01)
  *A42B 3/06* (2006.01)
  *A42B 3/04* (2006.01)
  *A42B 1/245* (2021.01)
  *A42B 1/242* (2021.01)
  *A42B 1/241* (2021.01)

(52) U.S. Cl.
  CPC .............. *A42B 3/0433* (2013.01); *A42B 3/06* (2013.01); *A42B 3/30* (2013.01); *A61B 5/6803* (2013.01); *A61B 2562/0219* (2013.01)

(56) References Cited

U.S. PATENT DOCUMENTS

| | | | |
|---|---|---|---|
| 2006/0059606 A1 | 3/2006 | Ferrara | |
| 2008/0256686 A1 | 10/2008 | Ferrara | |
| 2012/0233745 A1 | 9/2012 | Veazie | |
| 2013/0303946 A1* | 11/2013 | Gettens | A61B 5/11 600/587 |
| 2014/0020158 A1 | 1/2014 | Parsons et al. | |
| 2014/0173812 A1* | 6/2014 | Krueger | A41D 13/015 2/455 |
| 2017/0089779 A1* | 3/2017 | Dantus | A61B 5/369 |

OTHER PUBLICATIONS

Radovitzky et al. An animal-to-human scaling law for blast-induced traumatic brain injury risk assessment. PNAS Oct. 28, 2014 vol. 111 No. 43. (pp. 15310-15315). [retrieved on Nov. 30, 2020], Retrieved from <https://www.pnas.org/cgi/doi/10.1073/pnas.1415743111>.

* cited by examiner

SYSTEMS AND DEVICES FOR DETECTING, LOCATING AND MITIGATING CONCUSSIVE IMPACT FORCES

This application claims the benefit of U.S. Provisional Application Ser. No. 62/761,974 filed Apr. 16, 2018, which is hereby incorporated herein by reference.

TECHNICAL FIELD

The embodiments disclosed herein relate to protective headwear and, in particular, to systems and devices for detecting, locating and mitigating concussive impact forces, and providing for data-mining of such impacts with sufficient detail to support medical research into new diagnostic and treatment protocols.

BACKGROUND

Sports and other activities (e.g. employment) that involve a risk of high-impact hits to the head typically require participants to wear protective helmets to minimize the risk of serious head injury such as but not limited to concussions.

Existing protective helmets generally include an outer shell made of a hard material and an inner liner arranged on the inner side of the outer shell. The inner liner is generally made of a soft material and, in some cases, functions as a shock-absorbing system that absorbs an impact force directed towards the head of a wearer of the helmet.

Existing protective helmets and ancillary devices have many disadvantages. First, existing protective helmets and ancillary devices suffer from a limited ability to absorb hard impacts that lead to head and brain injuries of wearers. Second, existing protective helmets and ancillary devices lack effective systems for detecting the strength, direction and positioned of concussive impact forces. Third, existing helmets and ancillary devices have no mechanism to adequately alert the wearer, or those around them (e.g. a companion, co-participant, coach, trainer, referee, etc.) that the wearer has suffered a potentially concussion force injury and should be withdrawn from the activity and provided with medical attention to confirm if such an injury has occurred. This lack of signal can lead to a second impact, triggering "Second Impact Syndrome", significantly increasing the risk of serious injury.

Accordingly, there is a need for improved systems and devices for detecting, locating and mitigating concussive impact forces.

SUMMARY

Systems and devices for wearing on a wearer's head for detecting, locating and mitigating concussive impact forces are described herein. According to at least one aspect, the devices include a base configured to conform to the wearer's head and retain a plurality of pouches on an outer surface of the base. The plurality of pouches are configured to absorb at least a portion of an impact force directed towards the outer surface of the base, provide an indication when the impact force directed towards the outer surface of the base has a magnitude exceeding a concussion-indicating level of force and provide a location of impact when the impact force directed towards the outer surface of the base has a magnitude exceeding the concussion-indicating level of force.

The base may have a plurality of receptacles arranged on an outer surface of the base, each receptacle of the plurality of receptacles being configured to retain a respective pouch of the plurality of pouches.

Each receptacle of the plurality of receptacles may define a pocket configured to retain a pouch against the outer surface of the base.

Each receptacle may define an opening and a pocket extending inwardly from the opening, the pocket configured to retain a pouch against the outer surface of the base.

The plurality of receptacles may be arranged in an array on the outer surface of the base to cover top, rear, left side and right side portions of the wearer's head when the wearer is wearing the device.

Each receptacle of the plurality of receptacles may be at least partially transparent to provide for an observer to see a pouch retained in each receptacle.

At least some of the receptacles of the plurality of receptacles may have a rectangular shape.

Each pouch of the plurality of pouches may have a width in a range of about 0.5 inches to about 1 inch.

Each pouch of the plurality of pouches may have a length in a range of about 0.5 inches to about 1 inch.

Each pouch of the plurality of pouches may include a resiliently flexible material enclosing a fluid.

Each pouch may be configured to rupture upon receiving an impact force having a magnitude exceeding a concussion-indicating level of force.

The receptacles may be arranged on the outer surface of the base to provide for the fluid to travel from one or more of the plurality of pouches to the base upon the one or more of the plurality of pouches receiving an impact force having a magnitude exceeding a concussion-indicating level of force.

The fluid may be a liquid or a gel having a viscosity in a range of about 85 to about 140 cP at 20° C.

The fluid may include a dye of a colour that contrasts a colour of the base.

The device may also include a processor coupled to the base, an accelerometer coupled to the base and communicatively coupled to the processor, the accelerometer configured to measure a direction and the magnitude of the impact force, a transmitter communicatively coupled to the processor, the transmitter to transmit the direction and the magnitude of the impact force to an external electronic device and a power source communicatively coupled to the processor and the transmitter to provide power to at least the processor and the transmitter.

According to another aspect, the device includes a base configured to conform to the wearer's head and an impact detection and absorption layer coupled to the base. The impact detection and absorption layer is configured to absorb at least a portion of an impact force directed against the outer surface of the base, provide an indication when the impact force directed against the outer surface of the base has a magnitude exceeding a concussion-indicating level of force and provide a location of impact when the impact force directed against the outer surface of the base has a magnitude exceeding a concussion-indicating level of force. The bursting of the pouch utilizes the First Law of Thermodynamics (Preservation of Energy) whereby the force that has penetrated the wearer's helmet and would in the absence of the device have been transferred through the wearer's skull to the brain, is instead as least partially dissipated by the fluid escaping from the pouch upon its bursting.

The impact detection and absorption layer may include a plurality of pouches and a plurality of receptacles arranged on an outer surface of the base, each receptacle configured to retain a pouch of the plurality of pouches against the outer surface of the base.

Each receptacle of the plurality of receptacles may define a pocket to retain a pouch of the plurality of pouches against the outer surface of the base.

Each receptacle may defines an opening and a pocket extending inwardly from the opening to retain a pouch of the plurality of pouches against the outer surface of the base.

According to another aspect, a system for detecting and mitigating concussive impact forces is described herein. The system includes at least one communication network and a device for wearing on a wearer's head, the device including a base configured to conform to the wearer's head and retain a plurality of pouches on an outer surface of the base, the plurality of pouches configured to: absorb at least a portion of an impact force directed towards the outer surface of the base; provide an indication when the impact force directed towards the outer surface of the base has a magnitude exceeding a concussion-indicating level of force; and provide a location of impact when the impact force directed towards the outer surface of the base has a magnitude exceeding a concussion-indicating level of force. The device also includes a processor coupled to the base; a three-axis accelerometer coupled to the base and communicatively coupled to the processor, the accelerometer configured to measure a direction and the magnitude of the impact force; a transmitter communicatively coupled to the processor, the transmitter to transmit the direction and the magnitude of the impact force to an external electronic device; and a power source communicatively coupled to the processor and the transmitter to provide power to at least the processor and the transmitter. The system also includes an external electronic device having at least one server communication interface operable to communicate with the device and at least one user computing device via the at least one communication network, a processing unit; and a storage unit to store the direction and the magnitude of the impact force.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
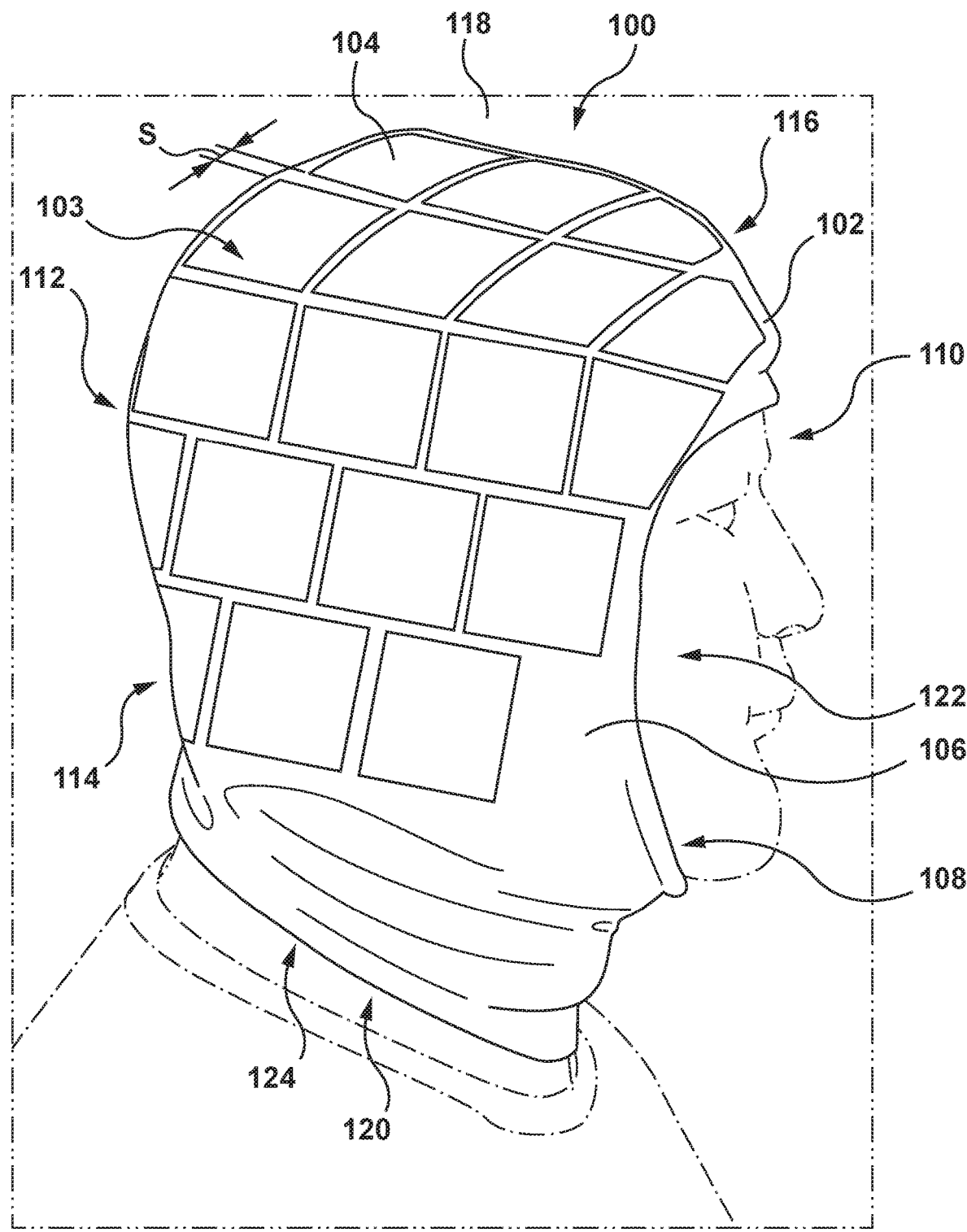
FIG. 1 is a side perspective view of a device for detecting, locating and mitigating concussive impact forces, in accordance with one embodiment.

The skilled person in the art will understand that the drawings, further described below, are for illustration purposes only. The drawings are not intended to limit the scope of the applicant's teachings in any way. Also, it will be appreciated that for simplicity and clarity of illustration, elements shown in the figures have not necessarily been drawn to scale. For example, the dimensions of some of the elements may be exaggerated relative to other elements for clarity. Further aspects and features of the example embodiments described herein will appear from the following description taken together with the accompanying drawings.

DETAILED DESCRIPTION

Various systems or devices will be described below to provide an example of each claimed embodiment. No embodiment described below limits any claimed embodiment and any claimed embodiment may cover systems or devices that differ from those described below. The claimed embodiments are not limited to systems or devices having all of the features of any one systems or devices described below or to features common to multiple or all of the systems or devices described below.

Terms of degree such as "about" and "approximately" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Generally, systems and devices for detecting, locating and mitigating concussion-inducing impact forces are described herein. The systems and devices described herein may detect when a concussion-inducing impact force has been received by a wearer of a device described herein, mitigate the effect of a concussion-inducing impact force on a wearer of a device described herein, and provide a location of a concussion-inducing impact force received on the head of a wearer of a device described herein.

Generally, concussion-inducing impact forces that can be detected and located using the systems and devices described include impacts that have a high risk of causing a head or brain injury and occur during activities where impacts to the head are likely to occur.

The systems and devices described herein generally include an impact absorption layer that provides for detecting, locating and mitigating concussive-inducing impact forces. For instance, in some embodiments, the impact absorption layer includes a plurality of fluid-filled pouches that provide for detecting, locating and mitigating concussive-inducing impact forces. Each of the pouches may be releasably coupled to a base that is fitted to conform to a wearer's head. For instance, in some embodiments, each of the pouches may be inserted into a pocket and retained against an outer surface of a balaclava-style hood that is fitted to conform to a wearer's head. In other embodiments, each of the pouches may be inserted into a pocket and retained against an outer surface of a skullcap similar to a swimmer's cap that is fitted to conform to a substantial portion of a wearer's head.

In the event that a potentially concussive-inducing impact force is received by the device when a wearer is wearing the device, and the impact is severe enough to potentially cause injury to the wearer's head or brain, one or more of the pouches of the systems or devices described herein may rupture or burst. The rupture of one or more of the pouches of devices described herein results in a fluid contained in the one or more pouches to be released from the pouch and transferred onto the base that conforms to the wearer's head. As the pouches are configured to rupture upon receiving a force exceeding a threshold for indicating a concussive-inducing impact force, the rupture of the one or more pouches indicates that a concussive-inducing impact force was received by the wearer of the device. Further, the rupture of the one or more pouches provides a precise position on the wearer's head where the concussive-inducing impact force was received. For instance, rupture of one or more of the pouches of the systems and devices described herein may correspond to the wearer receiving an impact beyond a threshold for a concussive-inducing impact force and that the wearer of the device described herein should seek medical attention. The release of the liquid is conspicuous to allow a coworker, coach, trainer, supervisor or other observer to notice its release, as the wearer may not be aware of the impact or choose to ignore it based on either bravado or ignorance. This signal will allow the third party to alert the wearer, and in the case of a coach or trainer, potentially prevent the wearer from returning the sport or activity where the rupture of the pouch was triggered. It is not uncommon for participants in some activities to attempt to hide potential concussive force injuries from their coach or trainer so as to not be withdrawn from the activity. This device will reduce the possibility of such cases of bravado exposes participants from further injury.

Further still, the one or more of the pouches of the devices described herein also mitigate at least a portion of a force (such as a concussive-inducing impact force) received by a wearer of the devices described herein by deforming upon receipt of an impact force and inhibiting the force of the impact from being directly received by the wearer's head.

The devices described herein may also include a three-axis accelerometer or the like, affixed closely to the skull of a wearer, that provides data on the exact force and a direction of impact upon a wearer receiving a concussive-inducing impact force. The accelerometer may be located on a portion of the head where there is little flesh between the skull and the surface of the skin (e.g. on the front of the head/front of the device) allowing the device to measure forces that reach the skull.

The wearer benefits from having some additional protection against impact force reaching the skull, a signal that they should seek medical attention and a personal database with a history of their head blows. The medical community, and by extension, head-injury patients, benefit from a comprehensive database to support the development of new diagnostic and treatment protocols for head injuries.

One mechanism for determining a threshold of a concussion-indicating force that indicates that a potentially serious impact has occurred is the Head Injury Criterion ("HIC"), which is already in use for the development of safety equipment in automobiles.

The HIC is a measure of the likelihood of head injury arising from an impact. The HIC is commonly used to assess safety related to vehicles, personal protective gear, and sport equipment. The HIC is defined as:

$$HIC = \left\{ \left[ \frac{1}{t_2 - t_1} \int_{t_1}^{t_2} a(t)dt \right]^{2.5} (t_2 - t_1) \right\}_{max}$$

where $t_1$ and $t_2$ are the initial and final times (in seconds) of the interval during which HIC attains a maximum value, and acceleration a is measured in gs (standard gravity acceleration). The maximum time duration of HIC, $t_2-t_1$, is limited to a specific value between 3 and 36 ms, usually 15 ms. This means that the HIC includes the effects of head acceleration and the duration of the acceleration. Large accelerations may be tolerated for very short times. Some studies have found that concussions occur at HIC=250 in most athletes.

Another mechanism for determining a concussion-indicating force that indicates that a potentially serious impact has occurred is measuring the intensity of the dynamic loads directed upon the head. Previous studies such as but not limited to *Rodent Model of Direct Cranial Blast Injury* (Kuehn, Simard, et all) from the October 2011 Journal of Neurotrauma and Radovitzky et al. from the National Academy of Sciences of the United States of America, *An animal-to-human scaling law for blast-induced traumatic brain injury risk assessment* (October 2014) have attempted to clarify the understanding of brain injury due to intense dynamic loads. Based on these and other studies, a generally accepted threshold range for indicating that dynamic loads directed upon the head have a potentially serious impact is about 20 to about 30 psi, or about 23 to about 27 psi, or about 24 PSI.

The systems and devices described herein may provide comprehensive data on the location, direction and force of an impact to the skull, such data to be collected via integrated communication technology and user interaction to create a comprehensive and historical database specific to each wearer's history of head trauma, as well as creating an anonymous collective database for the medical community to develop improved diagnostic and treatment protocols based.

Turning now to the Figures, FIG. 1 shows a side perspective view of a device 100 for detecting, locating and mitigating concussive impact forces, in accordance with one embodiment. Device 100 includes a base 102 and an impact detection and absorption layer 103. In some embodiments, the base 102 and the impact and absorption detection layer 103 can be integral with each other. In other embodiments, such as the embodiment shown in FIG. 1, base 102 and an impact detection and absorption layer 103 are separate and coupled to each other. In the embodiment shown in FIG. 1, impact and adsorption layer 103 is configured to retain a plurality of pouches 104 that cover at least a portion of an outer surface 106 of the base 102. In the embodiment shown in FIGS. 2-4, impact and adsorption layer 203 includes a plurality of receptacles 209. Therein, each receptacle 209 is configured to retain one of the plurality of pouches 204.

Returning to FIG. 1, base 102 is made of a flexible material to provide for base 102 to substantially conform to at least a portion of a wearer's head. Base 102 has a front side 110, a rear side 112, opposing left and right sides 114 and 116, respectively, and opposing top and bottom sides 118 and 120, respectively. In the embodiment shown in FIG.

1, base 102 is a balaclava-style hood and defines an inner cavity 108 configured to receive a wearer's head. Cavity 108 is sized such that a wearer's head is snugly and comfortably nestled within the cavity 108 and surrounded by the base 102 when the wearer wears the device 100.

Base 102 generally extends from top side 118 where it covers a top portion of the wearer's head downwardly along rear side 112. In the embodiment shown in FIG. 1, the base 102 extends downwardly along the rear side 112 so that the base 102 at least partially covers the wearer's neck. Pouches 104 are arranged on the rear side 112 to substantially cover a back portion of the wearer's head.

Base 102 generally also extends from top side 118 downwardly along the left and right sides 114, 116. In the embodiment shown in FIG. 1, the base 102 extends downwardly along the left and right sides 114, 116 so that the base 102 covers the wearer's ears and at least a portion of the wearer's neck. In some embodiments, the device described herein covers at least the frontal, parietal temporal and occipital bones of the wearer's skull when worn by the wearer.

Front side 110 includes a first opening 122 sized and shaped to provide for a wearer's face to be exposed through the first opening 122 when the base 102 is worn on the wearer's head and bottom side 120 includes a second opening 124 sized and shaped to receive the wearer's head into cavity 108 when the wearer wears the device 100.

Figure 2:
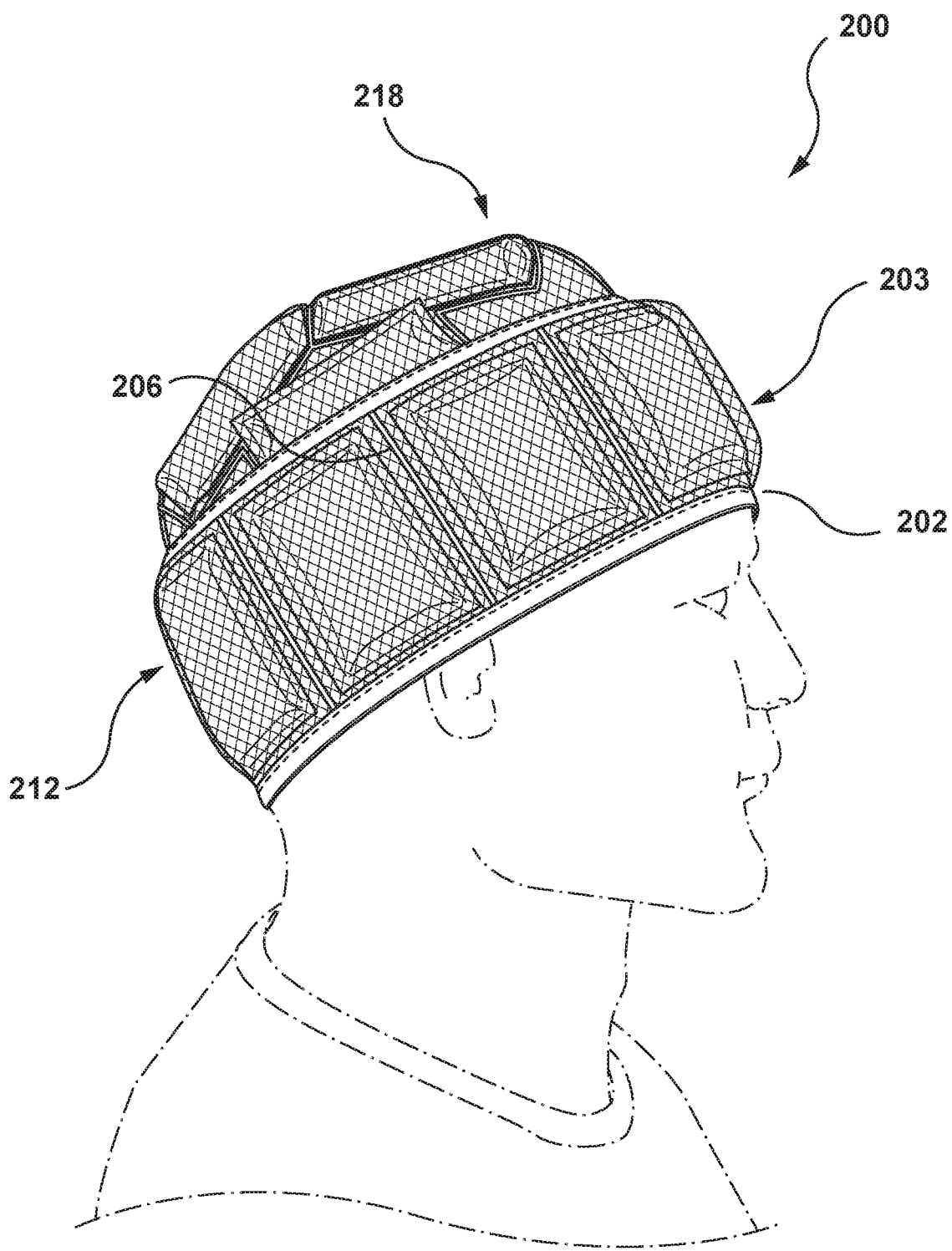
FIG. 2 is a side perspective view of a device for detecting, locating and mitigating concussive impact forces, in accordance with another embodiment.

In another embodiment, FIG. 2 shows a device 200 including a base 202. Certain elements of the device 200 that are similar to those in device 100 are referred to using like reference numerals, incremented by 100. To avoid repetition, the similar elements are not discussed in as much detail. Unless otherwise stated below, all the teachings disclosed herein with relation to the device 100 can apply to the device 200 as well.

Figure 3:
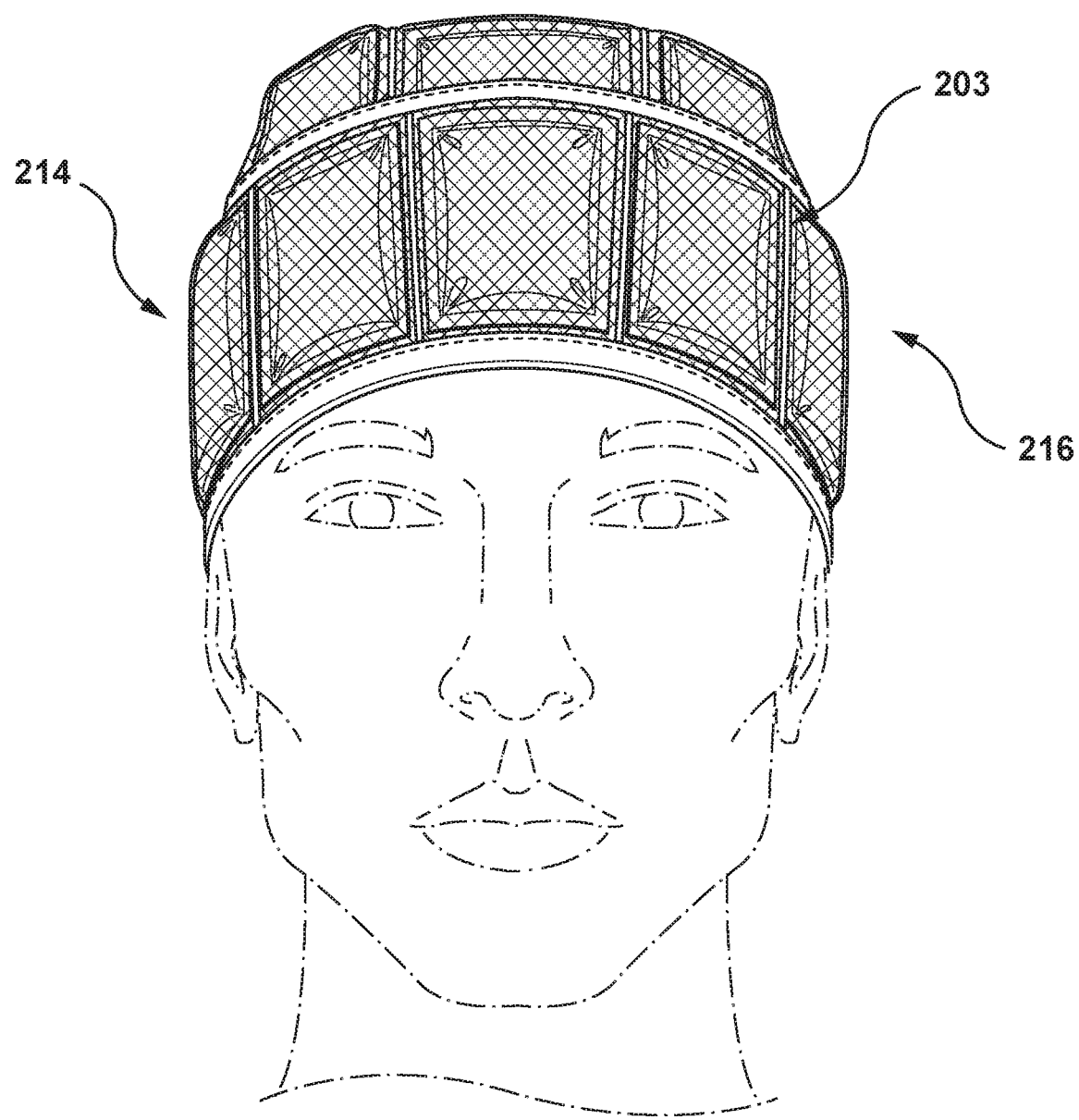
FIG. 3 is a front view of the device for detecting, locating and mitigating concussive impact forces of FIG. 2.
Figure 4:
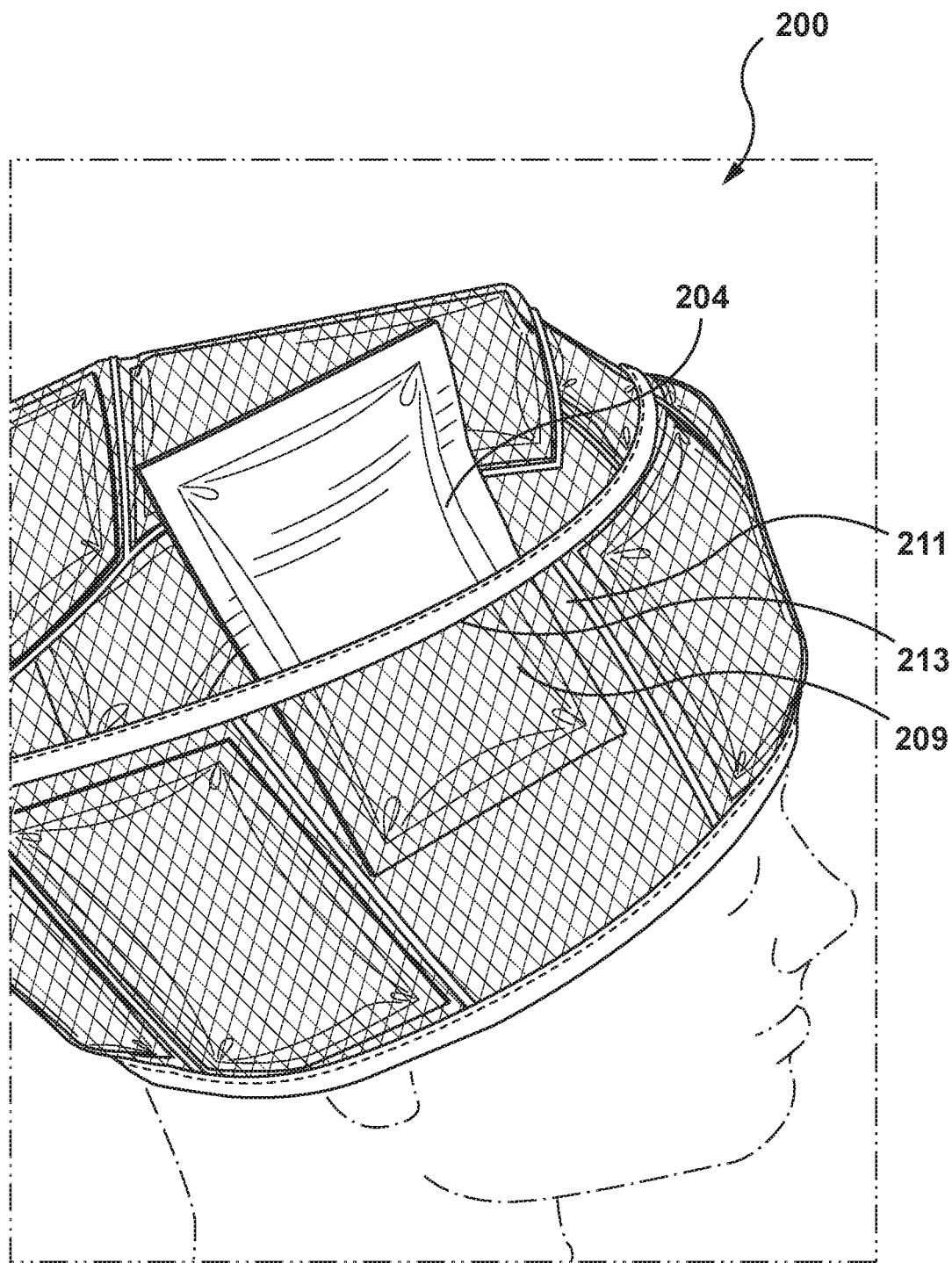
FIG. 4 is an elevated perspective view of the device for detecting, locating and mitigating concussive impact forces of FIG. 2 showing a pouch being removed from a receptacle of the device.

In the embodiment shown in FIGS. 2-4, base 202 extends downwardly along the rear side 212 at least to or below the parietal bones of the wearer's skull. In the embodiment shown in FIG. 2, the base 202 extends downwardly along the left and right sides 214, 216 (see FIG. 3), respectively, at least to or below the wearer's ears.

The impact detection and absorption layer described herein is configured to retain a plurality of pouches positioned on at least a portion of an outer surface of the base. For instance, in the embodiment shown in FIGS. 2-4, impact detection and absorption layer 203 includes a plurality of receptacles 209 for retaining a plurality of pouches 204 against an outer surface 206 of the base 202.

The receptacles 209 shown in FIG. 2 define an inner pocket 211 (see FIG. 4) and include an opening 213 configured to receive at least one of the plurality of pouches 204. Opening 213 may be oriented upwardly to inhibit a pouch from falling out of the pocket 211. Each receptacle 209 is made from a flexible material that provides for a pouch retained in pocket 211 to be visible to an observer. For instance, each receptacle 209 may be a screen that retains a pouch in pocket 211 and provides for a pouch retained in pocket 211 to be visible to an observer.

Opening 213 may include a fastener (not shown) to releasable close the opening 213 and retain a pouch in pocket 211.

Receptacles 209 are generally arranged in an array on the outer surface 206 of base 202 to substantially cover a top side, rear side, left side and right side of the wearer's head when the wearer wears the base 202. In some embodiments, the receptacles 209 are arranged in an array on the outer surface 206 of base 202 to substantially cover the outer surface 206 of the base 202.

Receptacles 209 are generally arranged on the base 202 such when each receptacle 209 retains at least one of the plurality of pouches 204, the plurality of pouches 204 sufficiently covers the outer surface 206 of the base 202 such that an impact force directed towards the wearer's head would impact one or more of the plurality of pouches 204 before impacting the base 202. The receptacles 209 (and pouches 204 therein) are arranged on the base 202 to extend from top side 218 where they cover the wearer's head downwardly along rear side 212 at least to or below the parietal bones of the wearer's skull. In the embodiment shown in FIG. 1, the pouches 104 extend downwardly along the rear side 212 so that the base 102 at least partially covers the wearer's neck.

The receptacles 209 generally also extend from top side 218 downwardly along the left and right sides 214, 216, respectively, at least to or below the wearer's ears. In the embodiment shown in FIG. 1, the plurality of pouches 104 extends downwardly along the left and right sides 114, 116 so that the plurality of pouches 104 cover the wearer's ears and cover at least a portion of the wearer's neck.

In the embodiments shown in the Figures, many of the pouches 104 have a rectangular shape, while others are triangular or trapezoidal. Each pouch 104 may have any shape including but not limited to a circular shape, a square shape, a rectangular shape or any other polygonal shape. In some embodiments, each pouch 104 may have a length and/or a width in a range from about 0.5 inches to about 1 inch. In other embodiments, each pouch 104 may have a length and/or a width in a range from about 1 inch to about 2 inches. In other embodiments, each pouch 104 may have a length and/or a width in a range from about 0.1 inches to about 0.5 inches. In other embodiments, each pouch 104 may have a length and/or a width in a range from about 2 inches to about 4 inches.

In some embodiments, the receptacles 109 may be configured to have a shape that mimics the shape of pouches 104 to minimize spacing between neighboring pouches 104 when the pouches 104 are retained in pockets 111.

Impact detection and absorption layer 103 is configured to absorb at least a portion of a force directed towards a head of a wearer of base 102. Specifically, each pouch 104 is configured to absorb at least a part of an impact directed towards the wearer's head when the wearer is wearing device 100.

Each pouch 104 is configured to be deformable. For instance, in the embodiment shown in FIG. 1, each of the plurality of pouches 104 is formed from a resiliently flexible material, such as but not limited to plastic or rubber. Each of the pouches 104 also enclose a fluid that is configured to substantially fill the pouches 104. Each of the pouches 104 is resiliently flexible over a wide range of temperatures. Compression of the pouches 104 provides for the pouches 104 to absorb at least a substantial amount of the energy of the impact force to mitigate the amount of the impact force that is received by the wearer's head. The fluid enclosed in the pouches 104 and the resiliently flexible material provides for the pouches 104 to compress in the direction of an impact force when an impact force is received by the device 100. Upon receiving an impact force, each pouch 104 is configured to deform to absorb the energy of the impact force and inhibit the energy of the impact for from being received by the wearer's head. In some embodiments, different fluids can be enclosed in different pouches to provide for different areas of the device to withstand impact forces before the pouches 104 will rupture.

The pouches 104 can be configured to control the amount of deformation that the pouches experience before they rupture. For instance, in some embodiments the density of the resiliently flexible material forming the pouches 104 can be controlled to provide for controlling the deformation of the pouches 104 prior to rupture. In other embodiments, the viscosity of the fluid enclosed in each of the pouches can be controlled to control the deformation of the pouches 104 prior to rupture.

Generally, the thickness of the pouches 104 and the volume and viscosity of the fluid retained therein are three variables that may affect the amount of force required to rupture each pouch and how much force is dissipated by the gel disbursing. In some embodiments, each pouch may be calibrated to minimize "false negatives" (i.e. incidents where a concussion-level force has been received by the wearer and none of the plurality of pouches 104 burst). Correspondingly, a false positive refers to an incident where one or more of the pouches 104 burst but concussion-level force has been received by the wearer.

In some embodiments, the fluid retained in each pouch of the plurality of pouches 104 is a liquid such as but not limited to water. In other embodiments, the fluid may be a gel such as but not limited to a water soluble, washable, non-toxic, non-irritating highly viscous liquid (e.g. polyethylene glycol, other non-toxic and water-soluble substances, and dye). In some embodiments the fluid has a viscosity in a range of about 85 cP to about 140 cP at 20° C. In some embodiments, the fluid is pigmented with a colour that contrasts with the colour of the base 102 to provide for the fluid to be visible on the base 102 when a pouch ruptures or bursts.

Each pouch of the plurality of pouches 104 is spaced from a neighboring pouch of the plurality of pouches 104 by a spacing S to provide for each pouch of the plurality of pouches 104 to deform upon receiving an impact thereon and increase its surface area within the layer 103 without contacting a neighboring pouch of the plurality of pouches 104. By deforming, each pouch of the plurality of pouches 104 may absorb at least a portion of an impact force directed against the outer surface of the base 102 (e.g. directed towards the wearer's head when the wearer is wearing the device 100).

In some embodiments, at least some of the pouches of the plurality of pouches 104 are configured to burst or rupture upon receiving a concussion-indicating force (e.g. a force having a magnitude of about 24 psi). In some embodiments, all of the pouches of the plurality of pouches 104 are configured to burst or rupture upon receiving a concussion-indicating force (e.g. a force having a magnitude of about 24 psi).

Upon receiving a concussion-indicating force, each pouch 104 is configured to rupture and/or burst and thereby provide a location (e.g. on the outer surface 106 of the base 102) where the concussion-indicating force has been received by the wearer. Rupture of one or more pouches 104 has a two-fold significance.

In some embodiments, the pouches described herein may provide temperature control for a wearer of the devices described herein. For example, when the temperature of a person's head increases, it swells. The pouches described herein are generally positioned between a wearer's head and an overlying helmet (e.g. in applications where the wearer is wearing a helmet) and the pouches (e.g. the gel enclosed by each pouch) may absorb heat from the wearer's head to provide for cooling of the wearer's head.

Turning back to FIGS. 2-4, illustrated therein is another embodiment of a system 200 for detecting and mitigating concussive impact forces. In this embodiment, base 202 is has a shape that is similar to a swimmer's skullcap.

In this embodiment, base 202 generally extends from a top side 218 where it covers the wearer's head downwardly along rear side 212 so that the base 202 at least partially covers the wearer's neck. Base 202 also extends from top side 218 downwardly along the left and right sides 214, 216, respectively, to or below the wearer's ears. In the embodiment shown in FIG. 1, the base 102 extends downwardly along the left and right sides 114, 116 so that the base 102 covers ears and at least a portion of the wearer's neck. In the embodiment shown in FIGS. 2-4, front side 210 does not include a first opening and a second opening, as described with respect to FIG. 1.

The plurality of pouches 204 generally extend from top side 218 where they cover the wearer's head downwardly along rear side 212 so that the base 202 at least partially covers the wearer's neck. The plurality of pouches 204 also extend from top side 218 downwardly along the left and right sides 214, 216, respectively, so that the plurality of pouches 204 cover the wearer's ears and cover at least a portion of the wearer's neck.

Figure 5:
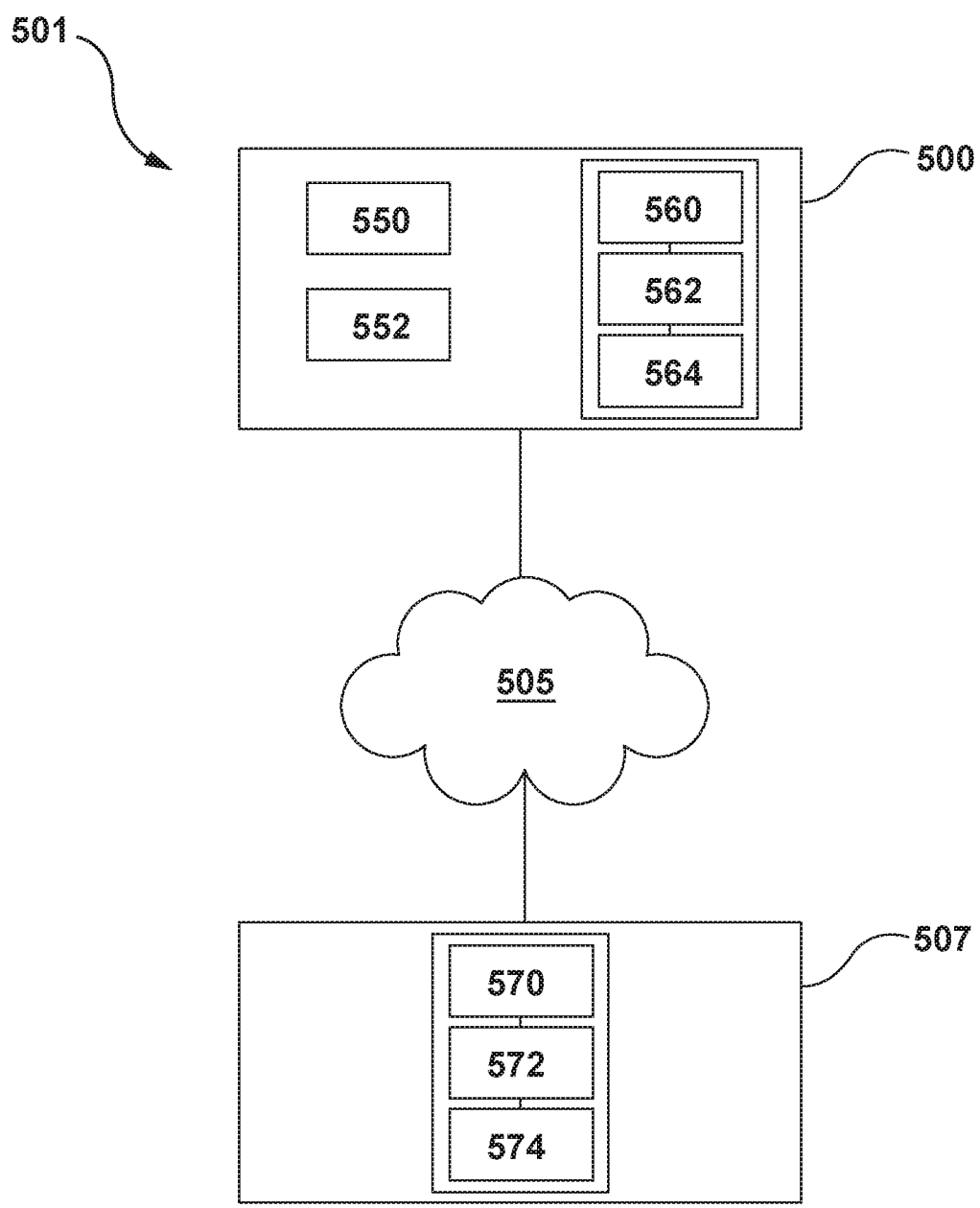
FIG. 5 is a block diagram of a system for detecting, locating and mitigating concussive impact forces, in accordance with one embodiment.

The devices and systems described herein may further include one or more accelerometers, gyroscopes, and/or magnetometers (e.g., as part of an inertial measurement unit (IMU)) vibration, shock, impact, and any other appropriate inertial sensors (herein referred to as impact sensors) for obtaining information concerning the position (e.g., attitude) acceleration, orientation, angular velocity, and/or vibration of the device. In some embodiments, these sensors can be coupled with a peripherals interface (not shown). For instance, as shown in FIG. 5, the device 500 may include an accelerometer 550. The accelerometer may be positioned on any portion of the base of the devices described herein, including but not limited to on a front portion of the base (e.g. against a wearer's forehead).

The devices and systems described herein may also include a reference code (e.g. a QR code). For instance, as shown in FIG. 5, the device 500 may include a reference code 552. The reference code may be applied to an inner surface or an outer surface of the base. For instance, the reference code may be stitched onto the base.

In some embodiments, the devices described herein may be in communication (e.g. over a communication network) with an external electronic device. FIG. 5 is a block diagram illustrating a system 501 of a device 502 (e.g. a concussion detection and mitigation device) communicating with (e.g. over a communication network 505) an external electronic device 507 in accordance with embodiments described herein, according to one embodiment.

External electronic device 507 may be any external electronic device capable of receiving data from the device 500 according to the embodiments described herein. For example, the external electronic device 507 may be a portable computing device such as electronic tablet device, a personal computer, workstation, server, a desktop computer, a portable computer, a laptop, a mobile device, a personal digital assistant, a smartphone, a storage device, a portable media player, a portable electronic device, a wearable electronic device, or any combination of these. Electronic device 507 may include a display screen displaying a user interface for viewing by the user of the electronic device 507.

Electronic device 507 communicates with the device 500 via a network 505, which may be a Wi-Fi network, WiMAX, Zigbee, Z-Wave, Bluetooth™, Bluetooth™ Low Energy, near-field communication, or any other type of connection capable of providing uni-directional or bi-directional communication between the external electronic device 507 and the device 500.

As shown in FIG. 5, the device 500 can include a processing unit 560, a memory (or storage unit) 562 and a communication interface 564.

The processing unit 560 can include any suitable processors, controllers or digital signal processors that can provide sufficient processing power depending on the configuration, purposes and requirements of the device 500. In some embodiments, the processing unit 560 can include more than one processing unit with each processing unit being configured to perform different dedicated tasks.

The memory 562 can store data collected by the accelerometer 550 during the operation of the device 500. Example data can include motion tracking data and directional data collected by the accelerometer 550.

The communication interface 564 can include any component for facilitating communication with the other components of the system 501 via the communication network 505. For example, the communication interface 564 can include a wireless transceiver for communicating within a wireless communications network. The communication interface 564 can communicate identification data and/or operating data of the device 500 to the communication network 505. The communication interface 564 can receive commands from the communication network 505.

In some embodiments, the processing unit 564 can transmit data (e.g. motion data and/or directional data) from the device 500 to the external device 507 via the communication network 505. In some embodiments, the communication network 505 may include more than one communication network. In some embodiments, the processing unit 564 can transfer the data to the external device 507 in response to a trigger being generated by the processing unit 564. For example, the trigger can be generated in response to data (e.g. motion data and/or directional data) exceeding a threshold. For instance, in some embodiments, the device 500 can automatically transmit data to the external electronic device 507 upon the accelerometer collecting motion data that indicates that the device 500 received an impact force exceeding a threshold indicating that the impact force was a concussion-inducing impact force.

The device 500 may also include with an electrical energy storage unit (not shown) for supplying electrical power to components of device 500. Components of the device 500 that may require electrical power include but are not limited to the accelerometer 550. The electrical energy storage unit can be a battery. The battery can be disposable or rechargeable.

External electrical device 507 includes a storage unit 570, a processing unit 572, and a communication interface 574.

The storage unit 570 can store data generated by the processing unit 572 as well as data received from the device 500 and user computing devices (not shown). For example, the storage unit 570 can store data in respect of the operation of the system 501, such as authorization data.

Authorization data of the device 500 can relate to identification of who is authorized to access data collected by the device 500 and stored on the external electronic device 507. For instance, authorization data can be provided to the external electronic device via a QR code on the device 500. In some embodiments, the QR code may act as a "license plate" for their device, linking the device to a personal profile and history of head impacts stored on an external server In some embodiments, the QR code may provide for a physician treating a potentially injured wearer (e.g. a wearer that may be conscious or unconscious at the time) to access that wearer's head injury history via a medical community portal to the database.

While the above description provides examples of one or more systems or devices, it will be appreciated that other systems or devices may be within the scope of the claims as interpreted by one of skill in the art.

What is claimed is:

1. A protective headwear device for detecting, locating and mitigating a concussive impact force received by a wearer of the device, the protective headwear device comprising:
   a base configured to conform to the wearer's head and cover the wearer's head when the wearer is wearing the base, the base comprising:
   a plurality of receptacles covering an outer surface of the base; and
   a plurality of fluid-filled pouches, each pouch of the plurality of pouches:
   being positioned within a respective receptacle of the plurality of receptacles and releasably retained against the outer surface of the base by the respective receptacle;
   being removable from the respective receptacle after being ruptured by a concussion-indicating level of force;
   covering a respective surface area of the outer surface of the base, each respective surface area being at least 0.25 square inches, and each pouch having an impact surface area on the base that is less than 0.25 square inches, the impact surface area being configured to receive the impact force that causes the rupture of one or more pouches that cover at least 0.25 square inches to cause the rupture of one or more pouches that cover at least 0.25 square inches of the outer surface of the base and release of a conspicuous amount of fluid from the one or more pouches, the conspicuous amount of fluid providing a visual indication to an observer of the impact force that a magnitude of the impact force exceeds the concussion-indicating level of force; and
   being configured to:
   absorb at least a portion of the impact force directed towards the outer surface of the base when the magnitude of the impact force is less than the concussion-indicating level of force; and
   rupture and release the conspicuous amount of fluid when the magnitude of the impact force exceeds the concussion-indicating level of force.

2. The protective headwear device of claim 1, wherein each receptacle of the plurality of receptacles defines a pocket configured to releasably retain a respective pouch of the plurality of pouches against the outer surface of the base.

3. The protective headwear device of claim 1, wherein each receptacle defines an opening and a pocket extending inwardly from the opening, the pocket being configured to releasably retain a respective pouch of the plurality of pouches against the outer surface of the base.

4. The protective headwear device of claim 1 wherein the plurality of receptacles are arranged in an array on the outer surface of the base to cover at least a portion of frontal, parietal temporal and occipital bones of the wearer's skull when worn by the wearer.

5. The protective headwear device of claim 1, wherein at least a portion of each receptacle of the plurality of receptacles is at least partially transparent to provide for an observer to see a respective pouch of the plurality of pouches retained in each receptacle.

6. The protective headwear device of claim 1, wherein at least some of the receptacles of the plurality of receptacles are rectangular shaped receptacles.

7. The protective headwear device of claim 1, wherein a width of each pouch of the plurality of pouches is in a range of about 0.5 inches to about 1 inch.

8. The protective headwear device of claim 1, wherein a length of each pouch of the plurality of pouches is in a range of about 0.5 inches to about 1 inch.

9. The protective headwear device of claim 1, wherein each pouch of the plurality of pouches comprises a resiliently flexible material enclosing a fluid.

10. The protective headwear device of claim 9, wherein each pouch is further configured to rupture when the magnitude of the impact force exceeds the concussion-indicating level of force.

11. The protective headwear device of claim 9, wherein the each of the receptacles are arranged on the outer surface of the base to provide for the fluid to travel from one or more of the plurality of pouches to the base upon the one or more of the plurality of pouches receiving the impact force.

12. The protective headwear device of claim 9, wherein the fluid is a liquid or a gel with a viscosity in a range of about 85 to about 140 cP at 20° C.

13. The protective headwear device of claim 9, wherein the fluid includes a dye of a colour that contrasts a colour of the base.

14. A protective headwear device for wearing on a wearer's head, the protective headwear device comprising:
a base configured to conform to the wearer's head and cover the wearer's head when the wearer is wearing the base; and
an impact detection and absorption layer coupled to the base, the impact detection and absorption layer comprising:
a plurality of receptacles covering an outer surface of the base; and
a plurality of fluid-filled pouches, each pouch
being positioned within a respective receptacle of the plurality of receptacles and releasably retained against the outer surface of the base by the respective receptacle;
being removable from the respective receptacle after being ruptured by a concussion-indicating level of force;
covering a respective surface area of the outer surface of the base, each respective surface area being at least 0.25 square inches, and each pouch having an impact surface area on the base that is less than 0.25 square inches, the impact surface area being configured to receive the impact force that causes the rupture of one or more pouches that cover at least 0.25 square inches to cause the rupture of one or more pouches that cover at least 0.25 square inches of the outer surface of the base and release of a conspicuous amount of fluid from the one or more pouches, the conspicuous amount of fluid providing a visual indication to an observer of the impact force that a magnitude of the impact force exceeds the concussion-indicating level of force; and,
being configured to:
absorb at least a portion of the impact force directed against the outer surface of the base when the magnitude of the impact force is less than a concussion-indicating level of force; and;
rupture and release the conspicuous amount of fluid when the magnitude of the impact force exceeds the concussion-indicating level of force.

15. The protective headwear device of claim 14, wherein each receptacle of the plurality of receptacles defines a pocket to retain a pouch of the plurality of pouches against the outer surface of the base.

16. The protective headwear device of claim 14, wherein each receptacle defines an opening and a pocket extending inwardly from the opening to retain a pouch of the plurality of pouches against the outer surface of the base.

17. The protective headwear device of claim 1, wherein the first surface area is at least 1 square inch.

18. The protective headwear device of claim 1, wherein the first surface area is at least 2 square inches.

19. The protective headwear device of claim 14, wherein the first surface area is at least 1 square inch.

20. The protective headwear device of claim 14, wherein the first surface area is at least 2 square inches.

* * * * *